(12) United States Patent
Nease, Jr. et al.

(10) Patent No.: US 8,682,704 B2
(45) Date of Patent: Mar. 25, 2014

(54) METHODS AND SYSTEMS FOR SCHEDULING ACTIVITY LEVEL BASED MEETINGS

(75) Inventors: Robert F. Nease, Jr., St. Louis, MO (US); Katherine Harini Sundararaman, St. Louis, MO (US); John T. Reid, Wildwood, MO (US)

(73) Assignee: Express Scripts, Inc., St. Louis, MO (US)

( * ) Notice: Subject to any disclaimer, the term of this patent is extended or adjusted under 35 U.S.C. 154(b) by 0 days.

(21) Appl. No.: 13/315,542

(22) Filed: Dec. 9, 2011

(65) Prior Publication Data
US 2012/0173298 A1    Jul. 5, 2012

Related U.S. Application Data

(60) Provisional application No. 61/429,405, filed on Jan. 3, 2011.

(51) Int. Cl.
*G06Q 10/00*    (2012.01)

(52) U.S. Cl.
USPC ........................................ 705/7.19; 705/7.18

(58) Field of Classification Search
USPC .................................... 705/7.19, 7.18
See application file for complete search history.

(56) References Cited

U.S. PATENT DOCUMENTS

| | | | |
|---|---|---|---|
| 5,303,165 A * | 4/1994 | Ganz et al. | 356/319 |
| 5,722,418 A * | 3/1998 | Bro | 600/545 |
| 5,937,387 A * | 8/1999 | Summerell et al. | 705/2 |
| 6,039,688 A * | 3/2000 | Douglas et al. | 600/300 |
| 6,208,974 B1 | 3/2001 | Campbell et al. | |
| 6,569,094 B2 * | 5/2003 | Suzuki et al. | 600/300 |
| 6,605,038 B1 * | 8/2003 | Teller et al. | 600/300 |
| 7,024,369 B1 * | 4/2006 | Brown et al. | 705/2 |
| 7,337,123 B2 * | 2/2008 | Dvorak et al. | 705/7.19 |
| 7,647,285 B2 | 1/2010 | Heckerman et al. | |
| 7,743,098 B2 * | 6/2010 | Anglin et al. | 709/204 |
| 7,895,240 B2 * | 2/2011 | Dhayalan et al. | 707/802 |
| 8,027,822 B2 * | 9/2011 | Turgiss et al. | 703/11 |
| 8,070,655 B1 * | 12/2011 | Napolitano et al. | 482/8 |
| 8,121,953 B1 * | 2/2012 | Orttung et al. | 705/52 |
| 8,140,370 B2 * | 3/2012 | Larsen et al. | 705/7.19 |
| 8,180,663 B2 * | 5/2012 | Tischhauser et al. | 705/7.19 |
| 8,352,296 B2 * | 1/2013 | Taneja et al. | 705/5 |
| 8,359,208 B2 * | 1/2013 | Slutzky et al. | 705/3 |
| 8,374,888 B2 * | 2/2013 | Earles et al. | 705/2 |

(Continued)

FOREIGN PATENT DOCUMENTS

WO    WO 2008030729 A2 *    3/2008    ............. G06F 17/40

OTHER PUBLICATIONS

Walking Meetings—Energize Body and Mind Center for Health Improvement, 2005.*

(Continued)

*Primary Examiner* — Scott L Jarrett
(74) *Attorney, Agent, or Firm* — Randy L. Canis

(57) ABSTRACT

Methods and systems for scheduling wellness based meetings are described. In one embodiment, meeting data associated with a meeting is accessed. A meeting type designation is received. The meeting type designation designates the meeting as a walking meeting, a standing meeting, or a sitting meeting. Updated meeting data based on the meeting data and the meeting type designation is stored. Other methods and systems are described.

17 Claims, 10 Drawing Sheets

(56) References Cited

U.S. PATENT DOCUMENTS

| | | |
|---|---|---|
| 2001/0039503 A1 | 11/2001 | Chan et al. |
| 2004/0006490 A1 | 1/2004 | Gingrich et al. |
| 2004/0034289 A1 | 2/2004 | Teller et al. |
| 2004/0131997 A1* | 7/2004 | McGuire et al. ............ 434/127 |
| 2005/0015281 A1* | 1/2005 | Clark et al. ........................ 705/2 |
| 2005/0228692 A1* | 10/2005 | Hodgdon ........................ 705/2 |
| 2005/0240438 A1* | 10/2005 | Day ................................. 705/2 |
| 2006/0064313 A1 | 3/2006 | Steinbarth et al. |
| 2006/0122474 A1* | 6/2006 | Teller et al. ................... 600/300 |
| 2006/0129643 A1* | 6/2006 | Nielson et al. ................ 709/206 |
| 2006/0187025 A1 | 8/2006 | Engstrom et al. |
| 2006/0200368 A1 | 9/2006 | Casey |
| 2007/0035403 A1 | 2/2007 | Krishna et al. |
| 2007/0100595 A1* | 5/2007 | Earles et al. ................... 703/13 |
| 2007/0122780 A1* | 5/2007 | Moon et al. ................... 434/236 |
| 2007/0276719 A1* | 11/2007 | Franco .............................. 705/9 |
| 2008/0040159 A1 | 2/2008 | Deegan |
| 2008/0131997 A1 | 6/2008 | Kim et al. |
| 2008/0133282 A1* | 6/2008 | Landar et al. ..................... 705/5 |
| 2008/0146334 A1* | 6/2008 | Kil ................................. 463/36 |
| 2008/0319788 A1 | 12/2008 | Ross |
| 2009/0089133 A1* | 4/2009 | Johnson et al. ................... 705/9 |
| 2009/0222519 A1 | 9/2009 | Boyd |
| 2010/0049541 A1 | 2/2010 | Pollard et al. |
| 2010/0100561 A1 | 4/2010 | Cooper et al. |
| 2011/0307562 A1* | 12/2011 | Chakra et al. ................. 709/206 |
| 2011/0320235 A1* | 12/2011 | Bak et al. ..................... 705/7.19 |
| 2012/0173263 A1 | 7/2012 | Nease, Jr. et al. |
| 2012/0293605 A1* | 11/2012 | Seferian et al. ............ 348/14.08 |

OTHER PUBLICATIONS

Hopkins, Jammie Mack, Understanding Key Players and Factors Involved in the Implementation of Physical Activity Push Strategies into Organizational Settings, University of California, Los Angeles, 2012.*

Office Exercise: How to burn calories while you work MayoClinic.com, May 17, 2009, Retrieved from Archive.org.*

Fitting Fitness Into a Busy Schedule American Heart Association, Jun. 13, 2010, Retrieved from Archive.org.*

Ryker, Shannon, Company-sponsored wellness programs pay benefits Tribune Business Weekly, Jun. 16, 2008.*

Pakdwick, Gordon et al., Special Edition Using Microsoft Outlook 2000 Que, May 12, 1999.*

HealthMedia, "Physical Activity," http://www.healthmedia.com/products/digitalcoachingprograms/move.htm [Mar. 29, 2011] downloaded May 31, 2012, pp. 1-2.

* cited by examiner

METHODS AND SYSTEMS FOR SCHEDULING ACTIVITY LEVEL BASED MEETINGS

CROSS-REFERENCE TO A RELATED APPLICATION

The present application claims the benefit of U.S. provisional patent application Ser. No. 61/429,405, entitled "Methods and Systems for Promoting and Increasing Participation in Healthcare Related Events and Programs" filed on 3 Jan. 2011, the entire disclosure of which is incorporated herein by reference.

FIELD

The field relates to meeting scheduling systems, and more particularly to the use of meeting scheduling systems for promoting wellness-related behaviors.

BACKGROUND

Calendaring and scheduling systems and programs are commonly used to schedule meetings, appointments, and the like. Such systems and programs allow users to define various parameters for meetings or appointments, such as the date and time of the meeting or appointment, as well as the location of the meeting or appointment. Additionally, calendaring and scheduling systems provide a mechanism for invitations to be sent to intended participants in meetings, as well as a mechanism to allow the intended participants to accept or decline the invitation, and, in some cases, propose alternative times and/or locations for a meeting.

DETAILED DESCRIPTION

Example methods and systems for promoting wellness-related behaviors are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a user may utilize a scheduling system to set appointments and to schedule meetings, for example, with other individuals. The systems and methods may generally utilize the scheduling system to promote wellness-related behaviors for the user and/or the other individuals of the scheduling system. In some embodiments, the wellness-related behaviors may include meetings that the user of the scheduling system may schedule via the scheduling system.

In some embodiments, the user of the scheduling system may be motivated to select an active meeting format during the process of scheduling the meeting. The active meeting format may include, for example, a walking meeting or a standing meeting. For example, the active meeting format may be selected as a meeting type designation attribute of the meeting. In some embodiments, the meeting type designation may include both active meeting type designation, such as a walking meeting or a standing meeting, and a non-active meeting type designation, such as a sitting meeting. Allowing the user of the scheduling system to elect an active meeting format may encourage the user to select an active meeting format, such as a standing meeting or a walking meeting, rather than a non-active meeting format. Even moderate amounts of activity resulting from standing and/or walking meeting may have an impact on the overall health and wellness of the user in the short term or over a longer time. An example of the scheduling system may include OUTLOOK by Microsoft Corporation. However, or other calendaring/scheduling systems may be used with the methods and systems.

In some embodiments, default meeting type designations may be provided. Default meeting type designations may be based on, for example, the number of participants and/or the duration of the meeting. In some embodiments, the default meeting type designations may be based on organization-defined rules. In some embodiments, the default meeting type designations may be based on user-defined preferences. In some embodiments, the selection of a meeting type designation may be required to complete the scheduling of a meeting.

Figure 1:
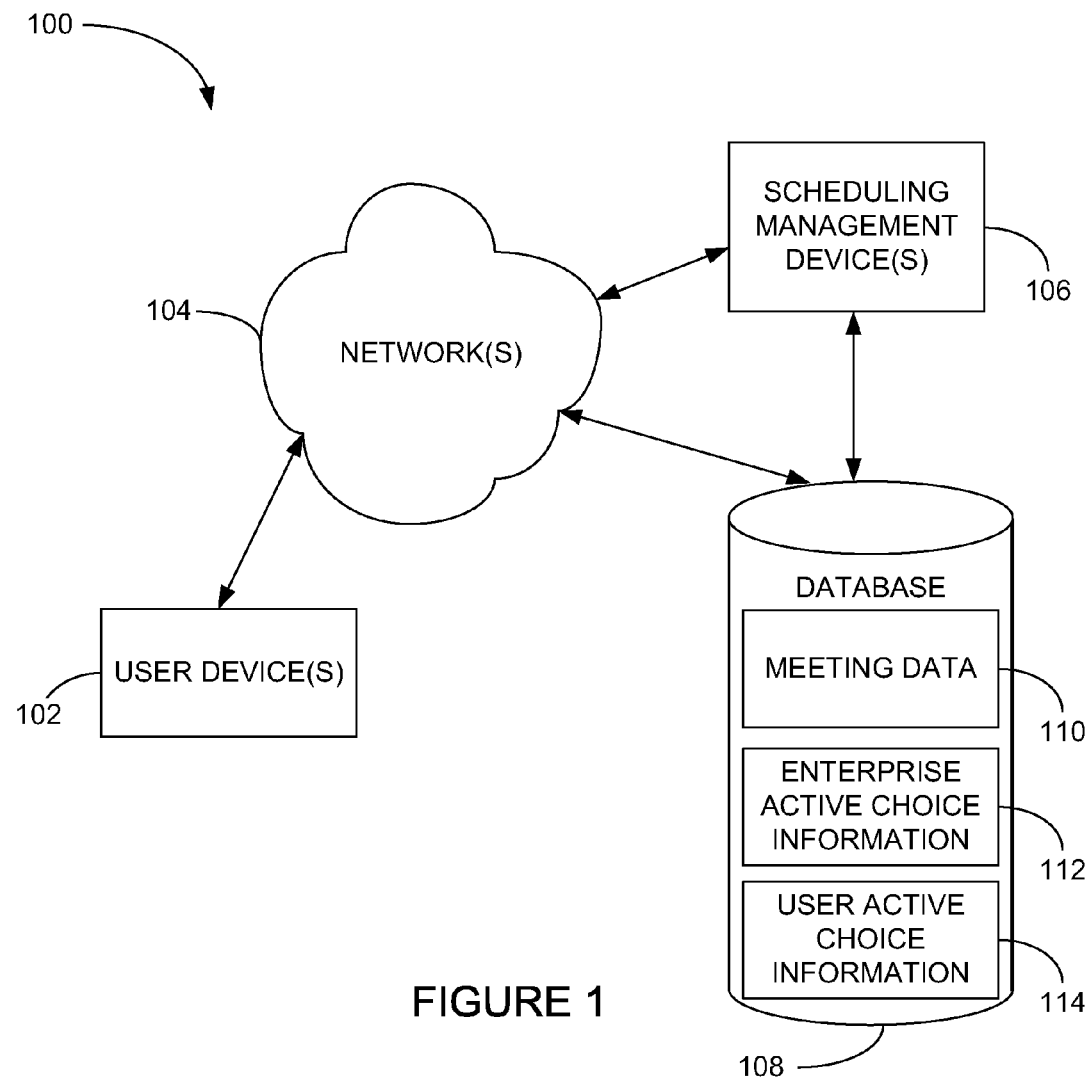
FIG. 1 is a block diagram of an example system, according to an example embodiment.

FIG. 1 is a block diagram of an example system 100, according to an example embodiment. The system 100 is an example embodiment in which a user may be able to schedule meetings having an active meeting format. The system 100 includes a user device 102 in communication with a scheduling management device 106 over a network 104.

The user device 102 is used by a device operator. The device operator may be a user of a scheduling system that enables meetings with other individuals to be scheduled. An example of a scheduling system may include OUTLOOK and/or EXCHANGE SERVER, both by Microsoft Corporation.

The user device 102 may be a stand-alone device that solely provides at least some of the functionality to enable the scheduling of meetings, or may be a multi-use device that has functionality outside of scheduling meetings as described herein. Examples of the user device 102 include a set-top box (STB), a receiver card, a mobile telephone, a personal digital assistant (PDA), a display device, a portable gaming unit, and a computing system; however other devices may also be used. In some embodiments, the computing system. For example, the user device 102 may include a mobile electronic device, such an IPHONE or IPAD device by Apple, Inc., mobile electronic devices powered by ANDROID by Google, Inc., and a BLACKBERRY device by Research In Motion Limited. The user device 102 also include other computing devices, such as desktop computing devices, notebook computing devices, netbook computing devices, gaming devices, and the like. Other types of electronic devices may also be used.

The network 104 by which the user device 102 communicates with the scheduling management device 106 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The scheduling management device 106 is a device operated by an entity at least partially responsible for facilitating scheduling of meetings for an organization and/or for facilitating scheduling of meetings for individuals. While the entity operating the scheduling management device 106 may include, for example, a corporate entity operating the scheduling management device 106 for the benefit of the corporate entity, other entities may operate the scheduling management device 106 either on behalf of themselves, the corporate entity, individuals, or another entity.

The user device 102 may be in a client-server relationship with the scheduling management device 106, a peer-to-peer relationship with the scheduling management device 106, and/or in a different type of relationship with the scheduling management device 106.

The scheduling management device 106 may be in communication directly (e.g., through local storage) and/or through the network 104 (e.g., in a cloud configuration or software as a service) with a database 108. The database 108 may be deployed on the user device 102, the scheduling management device 106, both the user device 102 and the scheduling management device 106, partially on the user device 102 and partially on the scheduling management device 106, on a separate device, or may otherwise be deployed. In some embodiments, there is a distinct database 108 for each user or organization, such that each organization's data may be stored and accessed separately. The database 108 may store meeting data 110, enterprise active choice information 112, and/or user active choice information 114.

The meeting data 110 includes information regarding meetings scheduled through the scheduling management device 106. In general, the meeting data 110 may include information about a meeting. The meeting data 110 may include information about a single meeting or multiple meetings. Example fields of the meeting data 110 include meeting topic, meeting date, meeting location, and meeting participants. For example, the meeting data 110 may include data such as the date on which the meeting is to occur, the time at which the meeting is to begin, the location where the meeting is to be held, the invited participants to the meeting, and the anticipated duration of the meeting. The meeting data 110 may include a device operator account identifier that identifies the device operator associated with the scheduling of a particular meeting. Additional data about, or attributes of, the meeting may also be included within the meeting data 110.

The enterprise active choice information 112 includes information regarding meeting type criterion, which may relate to rules regarding default meeting type designations for a given meeting parameter that may be applied across an organization, such as a corporation, a subdivision of a corporation such as a division or office, or the like. A single parameter or multiple parameters may be applied. The enterprise active choice information may be equally utilized in connection with organizations other than corporations, for example, non-profit organizations and the like. Examples of the enterprise active choice information 112 include default meeting type designations for all meetings, default meeting type designations based on anticipated meeting duration, default meeting type designations based on the number of meeting participants, and the like.

The user active choice information 114 includes information regarding meeting type criterion, which may relate to rules regarding default meeting type designations for given meeting parameters that may be applied to meetings scheduled by a particular user and/or that may be applied to meetings of which the particular user is a participant. Examples of the user active choice information 114 include default meeting type designations for all meetings, default meeting type designations based on anticipated meeting duration, default meeting type designations for based on the number of meeting participants, and the like.

In some embodiments, the device operator may schedule a meeting through user device 102. A meeting type designation may include, for example, a walking meeting, a standing meeting, or a sitting meeting, that may be selected via user device 102. The meeting type designation may be based on user selection, defaults associated with meeting type criterion, enterprise active choice information, user active choice information, or the like. The meeting type designation may be base on a single factor or multiple factors. With multiple factors, certain factors may take precedence over other factors.

While the system 100 in FIG. 1 is shown to include single devices 102, 106, multiple devices may be used. The devices 102, 106 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106 or in parallel to link the devices 102, 106.

Figure 2:
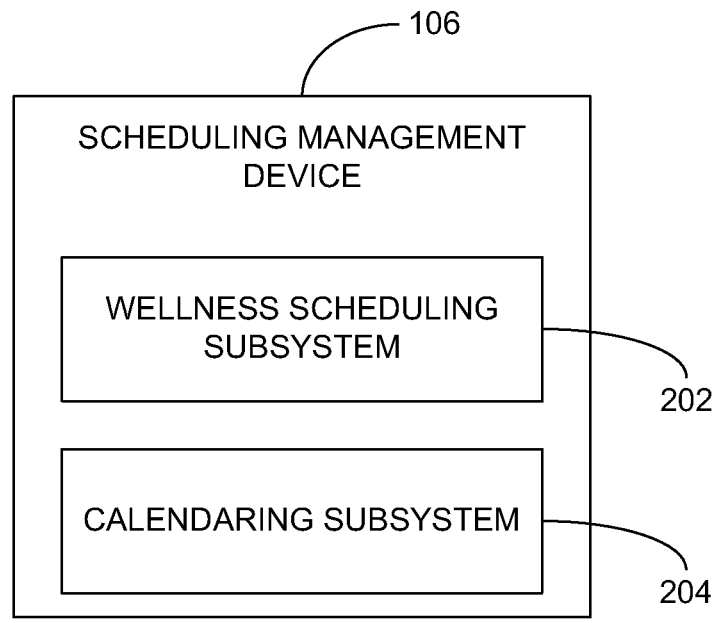
FIG. 2 is a block diagram of an example electronic device that may be deployed within the system of FIG. 1, according to an example embodiment.

FIG. 2 illustrates the user device 102, according to an example embodiment. The user device 102 may be used by a device operator to select a meeting type designation for a meeting. The user device 102 may be deployed in the system 100, or may otherwise be used.

The user device 102 may include a wellness scheduling subsystem 202, and/or a calendaring subsystem 204. The wellness scheduling subsystem 202 may enable the device operator of the user device 102 to select a meeting type designation. Examples of meeting type designations may include a walking meeting, a standing meeting, and a sitting meeting. In some embodiments, the calendaring subsystem 204 may enable a wellness-related or other type of event to be scheduled, for example, for an organization, such as a company, etc., including a defined group of individuals. The wellness-related event may include, for example, vaccinations, such as a flu shot, a health screening, a cholesterol screening, or other such event. One, or both, of the wellness scheduling subsystem 202 and the calendaring subsystem 204 may interact with, and/or be included as a module or component of, a calendaring/scheduling system, such as OUTLOOK and/or EXCHANGE SERVER, both by Microsoft Corporation.

In some embodiments, the calendaring subsystem 204 may generate or otherwise use a master calendar associated with the wellness-related event. In some embodiments, the calendaring subsystem 204 may schedule discrete appointments for individuals to participate in the event via the master calendar. The master calendar associated with the event may include multiple discrete potential appointments for the event. The multiple discrete potential appointments may be based on an event capacity. The event capacity may be based on the total duration of the event and the anticipated time for participation in the event by each individual. For example, an event may include the administration of flu shots. The flu shot event may extend for three days and may be available for three hours on each of the three days. As such, the total duration of the event may be nine hours. If it is anticipated that it will take ten minutes for each participating individual to receive a flu shot, the flu shot event may have a capacity including a total of 54 potential appointments. In some embodiments, the master calendar may include a greater number of potential appointments than the event capacity in anticipation of one or more scheduled individuals failing to keep scheduled appointments. In some embodiments, the master calendar may include a lesser number of potential appointments than the event capacity in anticipation of one or more individuals failing to accept the scheduling of an appointment.

The calendaring subsystem 204 may transmit appointment invitations (e.g., which may correspond to the potential appointments) to the defined group of individuals for the wellness-related event. For example, rather than only communicating to the defined group of individuals that the event is taking place and requesting that individuals schedule an appointment, the calendaring subsystem 204 may automatically schedule participation in the event by one or more individuals of the defined group of individuals, and may automatically transmit an appointment invitation to the individuals. In such an example embodiment, the calendaring subsystem 204 may automatically include the individuals as participants in the event, rather than requiring that the individuals seek to participate in the event of their own accord.

In an example embodiment, the appointment invitations may be transmitted to individuals in a tiered manner. For example, appointment invitations may first be sent to a first subset of the group of individuals that have been identified as having relatively more restricted schedules. The calendaring subsystem 204 may access calendar data associated with a scheduling/calendaring application, and may determine a relative schedule restriction for one, or more than one, individual. As such, the first subset may be determined, for example, based on the number of appointments scheduled for the group of individuals in a calendaring system, and therefore may be based on the relative availability of the individual. A time period for responding to the transmitted appointment invitation may be provided to the first subset of the group of individuals. Upon the expiration of the time period for responding, appointment invitations may be transmitted to a second subset of the group of individuals. The appointment invitations transmitted to the second subset of the group of individuals may be based on remaining available appointments for the event. The second subset of the group of individuals may include individuals identified as having relatively less restricted schedules, e.g., using the same or different criteria that were used to identify the first subset of the group of individuals. Additional subsets of the group of individuals may be utilized, and each subset may be provided with a time period for responding to the appointment invitation before appointment invitations are transmitted to the next subset of the group of individuals. In some embodiments, invitations may be transmitted to the group of individuals without utilizing tiered invitations. In some embodiments, an overlapping tiered invitation system may be used in which appointment invitations may be transmitted to the second subset of the group of individuals after the appointment invitations have been transmitted to the first subset of the group of individuals, but before the time period for replying has expired.

In an example embodiment, the appointment invitations may include a notification to an individual notifying the individual that they are scheduled to participate in the event on an indicated date at an indicated time. In some embodiments, the calendaring subsystem 204 may enable the individual to accept the invitation for the scheduled date and time, decline the invitation for scheduled date and time, request that the date and/or time be rescheduled to another date and/or time, or the individual may ignore the invitation and take no action. In some embodiments, the calendaring subsystem 204 may enable the individual to accept the invitation for the scheduled date and time, decline the invitation for the scheduled date and time, or request that the date and/or time be rescheduled. In such an embodiment, the calendaring subsystem 204 may enable the individual to affirmatively opt-out of the event by declining the scheduled appointment, but may not enable the individual to passively ignore the invitation. In some embodiments, the calendaring subsystem 204 may promote participation in the event (e.g., by presenting the option to decline the invitation in a smaller or less noticeable font), by presenting the option to decline the invitation as a multi-step process (e.g., requiring that a survey directed at the reason for opting out be completed in order to decline the scheduled invitation, through the use of a multi-layer menu system to decline the scheduled invitation, or other relatively complex process), or other mechanism that may increase the requirements for opting out of the event.

In some embodiments, if an individual requests that the date and/or time associated with the appointment invitation be rescheduled, the calendaring subsystem 204 may enable the individual to request a specific date and/or time for rescheduling the appointment for participation in the event. In some embodiments, the calendaring subsystem 204 may transmit a notification of available dates and times for rescheduling the appointment. In such an embodiment, the calendaring subsystem may enable the individual to select an available date and time for rescheduling the appointment. In some embodiments, responsive to the request to reschedule the appointment, the calendaring subsystem 204 may automatically generate a rescheduled appointment, and may transmit the rescheduled appointment to the individual requesting the rescheduling. In some such embodiments, the calendaring subsystem 204 may access calendar data for the individual, which may include information regarding appointments scheduled for the individual on a scheduling/calendaring system. The calendaring subsystem 204 may automatically generate a rescheduled appointment based on an indicated availability for the individual within the calendar data.

Figure 3:
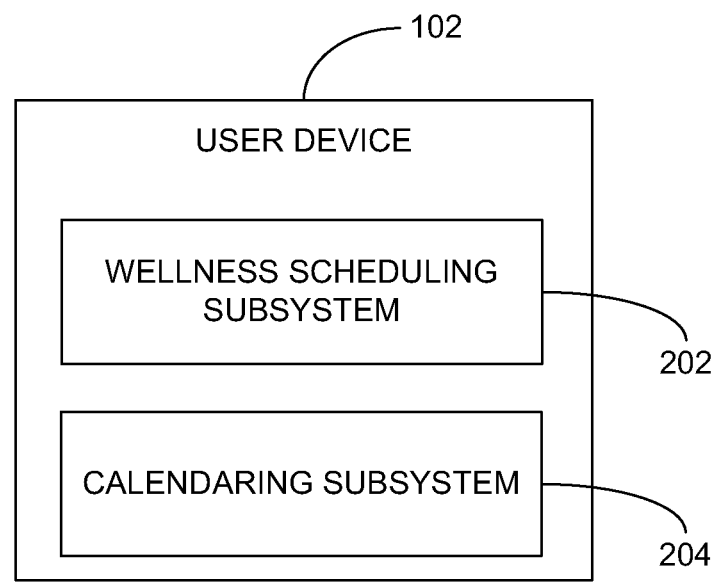
FIG. 3 is a block diagram of an example scheduling management device that may be deployed within the system of FIG. 1, according to an example embodiment.

FIG. 3 illustrates the scheduling management device 106, according to an example embodiment. The scheduling management device 106 may be deployed in the system 100, or may otherwise be used.

The scheduling management device 106 may include the wellness scheduling subsystem 202 and/or the calendaring subsystem 204. In some embodiments, the wellness scheduling subsystem 202, and the calendaring subsystem 204 when used may provide server-side functionality to the user device 102. By way of example, the wellness scheduling subsystem 202 and/or the calendaring subsystem 204 may be deployed in both the user device 102 and the scheduling management device 106. The user device 102 may then perform some of the functionality while other functionality is performed by the scheduling management device 106.

In some embodiments, the wellness scheduling subsystem 202 may include scheduling functionality that may enable the scheduling of meetings. In some embodiments, the wellness scheduling subsystem 202 may be incorporated into, or otherwise interact with, a scheduling application.

Figure 4:
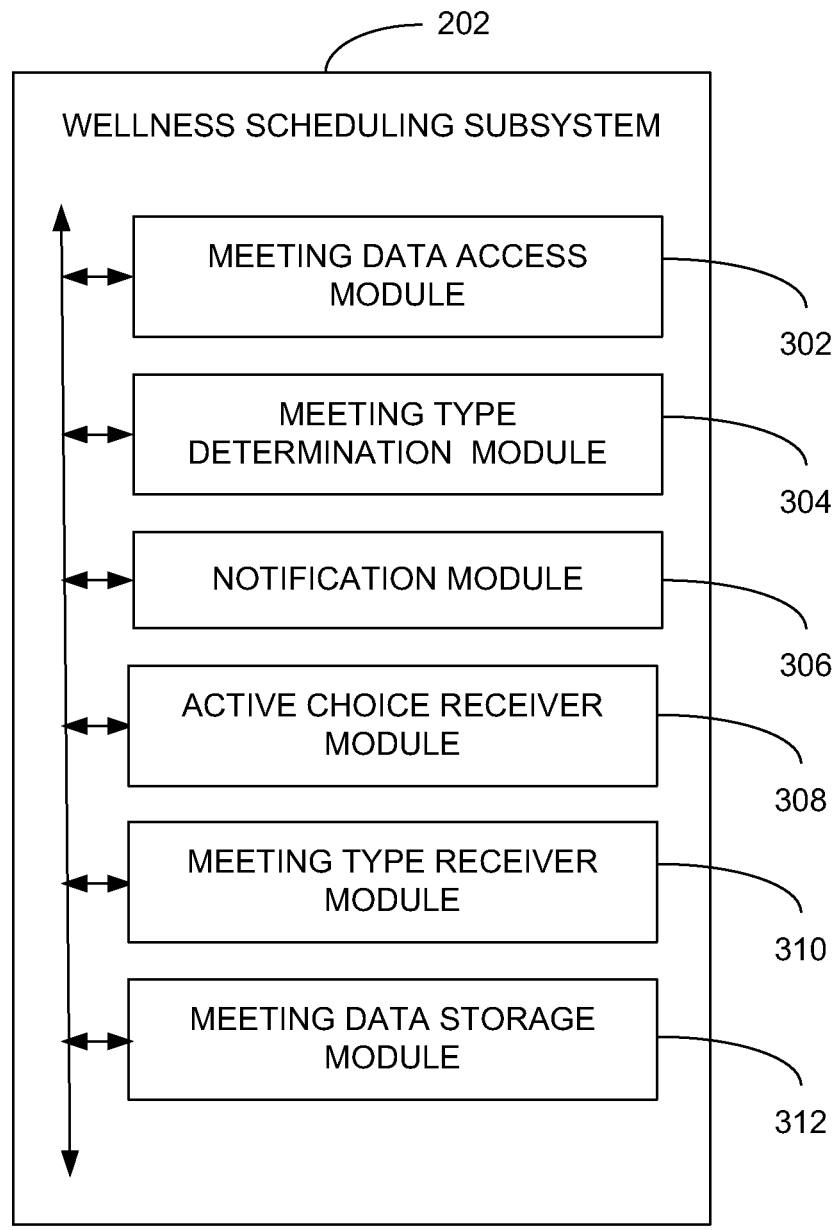
FIG. 4 is a block diagram of an example wellness scheduling subsystem that may be deployed within the electronic device of FIG. 2 or the scheduling management device of FIG. 3, according to an example embodiment.

FIG. 4 illustrates an example the wellness scheduling subsystem 202 that may be deployed in the user device 102, the scheduling management device 106, or otherwise deployed in another system. One or more modules are communicatively coupled and included in the wellness scheduling subsystem 202 to enable selection of a meeting type designation. The modules of the wellness scheduling subsystem 202 that may be included are a meeting data access module 302, a meeting type determination module 304, a notification module 306, an active choice receiver module 308, a meeting type receiver module 310, and a meeting data storage module 312.

In some embodiments, the modules of the wellness scheduling subsystem 202 may be distributed so that some of the modules are deployed in the user device 102 and some modules are deployed in the scheduling management device 106. In one embodiment, the modules are deployed in memory and executed by a processor coupled to the memory. The functionality contained within the modules 302-312 may be combined into a lesser number of modules, further divided among a greater number of modules, or redistributed among existing modules. Other configurations including the functionality of the modules 302-312 may be used.

Wellness-related behaviors may be promoted by the wellness scheduling subsystem 202. Wellness-related behaviors may include the use of active meeting formats. The use of active meeting formats may be promoted by bringing the option to conduct an active meeting format to the attention of a user, which may heighten the awareness of the user of such active meeting formats. Additionally, requiring the user to affirmatively select a meeting format, such as a relatively higher activity level format such as a walking meeting format or a standing meeting format, or a relatively lower activity level format such as a sitting meeting format, may motivate the user to select a relatively higher activity level meeting format. The active choice, or insistence that the user select a meeting format, may encourage the user to contemplate all available options and, potentially, subconsciously encourage the user to select a relatively higher activity level format.

In some embodiments, the meeting data 110 associated with a meeting that is being scheduled by the device operator of user device 102, or of a meeting that has previously been scheduled by the device operator of user device 102 may be accessed by meeting data access module 302. The meeting data 110 may be accessed by the meeting data access module 302 from the database 108, from the user device 102, from the scheduling management device 106, or may otherwise be accessed.

In some embodiments, the meeting data access module 302 may access the meeting data 110 by receiving data associated with the meeting. Receiving data associated with the meeting may include, for example, receiving data associated with the meeting as the meeting data is being defined (e.g., via a user interface that may be used to schedule the meeting). In some embodiments, receiving the meeting data 110 may include receiving the data associated with the meeting directly via the user device 102. In some embodiments, receiving the data associated with the meeting may include receiving the data associated with the meeting through the network 104 from the user device 102, from the scheduling management device 106, or from a different device.

In some embodiments, the meeting data access module 302 may access the data associated with the meeting by accessing the meeting data 110 from the database 108. The meeting data 110 stored within the database 108 may include data associated with a meeting that may have been defined (e.g., via a user interface that was used to schedule the meeting). The data associated with the meeting that was defined when the meeting what scheduled may have been stored in the database 108, for example, by the scheduling application that, in some embodiments, provides scheduling functionality.

A meeting type designation may be determined by the meeting type determination module 304. The meeting type designation may designate the meeting as a walking meeting, a standing meeting, or a sitting meeting. In some embodiments, the meeting type designation may be defined by the device operator of the user device 102 during scheduling of the meeting. For example, the user interface used to schedule the meeting may allow the device operator to select a meeting type option, or to otherwise define the meeting type to thereby provide a meeting type designation associated with the meeting. In some embodiments, the meeting type determination module 304 may determine that no meeting type designation has been received.

In an embodiment in which the meeting type determination module 304 may determine that no meeting type designation has been received, the notification module 304 may generate a notification based on the determination by the meeting type determination module 304 that no meeting type designation has been received. In some embodiments, the notification module 304 may generate a notification indicating that no meeting type designation has been determined associated with the meeting. In some embodiments, the notification module 304 may generate a notification requesting that a meeting type designation be selected (e.g., by the device operator of the user device 102 via a user interface used to schedule the meeting).

In some embodiments, the notification module 306 may generate a notification requesting that a meeting type designation be selected. The notification requesting that a meeting type designation be selected may include a suggested meeting type designation based on the meeting data 110 accessed by the meeting data access module 302 and based on a meeting type criterion. In some embodiments, the meeting type criterion may include a number of invited attendees at the meeting. In some embodiments, the meeting type criterion may include an anticipated duration of the meeting.

In some embodiments, the notification module 306 may generate a notification including a suggested meeting type designation that may be based on rules according to values associated with one, or more than one, meeting type criterion such as the number of invited attendees at the meeting and/or the anticipated duration of the meeting. The values associated with the one, or more than one, meeting type criterion may be determined based on the meeting data 110 accessed by the meeting data access module 302. For example, the notification module 306 may determine that the meeting includes three invited attendees at the meeting based on the meeting data 110. The notification module 306 may, therefore, determine a value of three for the meeting type criterion of the number of invited attendees at the meeting. Values for other meeting type criterion may be similarly determined (e.g., based on meeting data associated with the meeting).

In an example embodiment, the notification module 306 may generate a notification suggesting a walking meeting type designation for meetings having an anticipated duration less than thirty minutes, suggesting a standing meeting type designation for meetings having an anticipated duration less than one hour but longer than thirty minutes, and suggesting a sitting meeting type designation for meetings having an anticipated duration longer than one hour. In an example embodiment including a rule according to the number of invited attendees at the meeting, the notification module 306 may generate a notification suggesting a walking meeting type designation for meetings including three, or fewer, invited attendees at the meeting, suggesting a standing meeting type designation for meetings including between four and five invited attendees at the meeting, and suggesting a sitting meeting type designation for meetings including greater than five invited attendees at the meeting. Various rules including combinations of meeting type criterion, such as the number of invited attendees at the meeting or the anticipated duration of the meeting, and/or additional or alternative rules or meeting criterion may equally be utilized.

In some embodiments, the notification module 306 may generate a notification suggesting a meeting type designation based on rules that may be defined for an organization and/or may generate a notification suggesting a meeting type designation based on rules that may be defined for a single user and/or may be defined for a group of users. For example, in some embodiments, the active choice receiver module 308 may access the enterprise active choice information 112. The enterprise active choice information 112 may include rules or guidelines for meeting type designation based on meeting type criterion (e.g., such as the rules discussed above). The enterprise active choice information 112 may include rules that may be applicable to all and/or a subset of users within an organization, such as a corporation, club, or the like (e.g., who may use a common scheduling system). In some embodiments, the enterprise active choice information 112 may be defined, for example, by a system administrator or other individual within the organization and/or may be defined by an individual on behalf of the organization. The active choice receiver module 308 may access the enterprise active choice information 112, for example, by accessing the database 108 including the enterprise active choice information 112. One, or more than one, of the meeting type determination module 304, the notification module 306, and the active choice receiver module 308 may determine a default meeting type designation based on the meeting type criterion and the enterprise active choice information 112. In some embodiments, the notification module 306 may generate a notification requesting that a meeting type designation be selected, and which may suggest the default meeting type designation as the default meeting type designation based on one, or more than one, of the meeting data 110, the meeting type criterion, the and/or the enterprise active choice information 112.

In some embodiments, the active choice receiver module 308 may access user active choice information 114. The user active choice information 114 may include rules for meeting type designation based on meeting type criterion (e.g., such as the rules discussed above) that may be applicable to a single user, such as the device operator of the user device 102, and/or that may be applicable to a group of users. The user active choice information 114 may be defined by the user, and/or defined by an individual on behalf of the user or group of users, for example via preference or profile-type settings. The active choice receiver module 308 may access the user active choice information 114, for example, by accessing the database 108 including the user active choice information 114. One, or more than one, of the meeting type determination module 304, the notification module 306, and the active choice receiver module 308 may determine a default meeting type designation based on the meeting type criterion and the user active choice information 114. In some embodiments, the notification module 306 may generate a notification requesting that a meeting type designation be selected, and which may suggest the default meeting type designation as the default meeting type designation based on one, or more than one, of the meeting data 110, the meeting type criterion, the and/or the user active choice information 114.

In some embodiments, the meeting type determination module 304 may determine the meeting type designation based on the default meeting type designation, which may be based on the meeting type criterion and one, or more than one, of the enterprise active choice information 112 and the user active choice information 114.

The meeting type receiver module 310 may receive a meeting type designation associated with the meeting, which designates the meeting as a walking meeting type, a standing meeting type, or a sitting meeting type. In some embodiments, the meeting type receiver module 310 may receive the meeting type designation in response to the notification generated by the notification module 306. In an example embodiment, the meeting type receiver module 310 may receive the meeting type designation associated with the meeting based on a user selection. For example, the device operator of the user device 102 may select (e.g., via a user interface) a meeting type designation such as a walking meeting type designation, a standing meeting type designation, or a sitting meeting type designation. Other type of meeting type designations (e.g., automobile meetings, cycling/spinning meetings, running meetings, boot camp meetings, guitar-playing meetings, airplane meetings, etc.) may also be made depending on available meeting type designations. In some embodiments, custom meeting type designations may be made by users and/or others within or outside the organization.

In some embodiments, the meeting type receiver module 310 may access the default meeting type designation. The default meeting type designation may be accessed from one, or more than one, of the meeting type determination module 304, the notification module 306, and the active choice module. For example, if the device operator of the user device 102 does not select a meeting type designation, the meeting type receiver module 310 may access the default meeting type designation.

The meeting data storage module 312 may store updated meeting data based on the meeting type designation. The meeting data storage module 312 may store the updated meeting data in the database 110, on the user device 102, on the scheduling management device 106, and/or in a different location. In addition to other meeting data, the updated meeting data may include the meeting type designation determined by meeting type determination module 304 and/or the meeting type designation received by the meeting type receiver module 310.

In some embodiments, storing updated meeting data may include allocating resources for the meeting based on the meeting type designation. For example, in some embodiments, one, or more than one, walking spaces, such as a courtyard, a track, or the like, may be available to a corporation. In order to prevent overcrowding (that may, in some embodiments, diminish the ability to conduct a walking meeting), the number of individuals permitted in the walking space at the same time may be limited. In such an example, the meeting update module 312 may store updated meeting data including an allocation of a walking space for the date and time of a walking meeting. In another example, standing meeting spaces, such as an office or conference room not including chairs, may be made available by a corporation. In such an example, the meeting data storage module 312 may store updated meeting data including allocating a standing meeting space for the date and time of a standing meeting.

While the foregoing generally describes that the meeting data storage module 312 may stored updated meeting data, when the meeting data 110 has not been previously stored the meeting data storage module 312 may store the meeting data 110 based on the formatting of the methods and systems described herein. For example, the meeting data 110 may reflect operations performed by the subsystems of one or more of the modules of the wellness scheduling subsystem 202.

The wellness scheduling subsystem 202 may promote wellness-related behaviors, such as active meeting formats, by allowing individuals scheduling meetings to select an active meeting format as part of scheduling the meeting. In some embodiments, the wellness scheduling subsystem 202 may promote wellness-related behaviors by requiring or mandating that individuals scheduling meetings affirmatively select a meeting type designation for the meeting. In some embodiments, the wellness scheduling subsystem 202 may promote wellness-related behaviors by requiring individuals scheduling meetings to affirmatively select a meeting type designation, and by providing default meeting type designations that may encourage active meeting formats for some meetings, based on various meeting criteria.

In some embodiments, the wellness scheduling subsystem 202 may allow individuals and/or organizations to establish goals relative to wellness-related activities, such as active meeting formats. An example of a goal may include participating in a specified number of standing meetings per week and a specified number of walking meetings per week. The wellness scheduling subsystem 202 may, in some embodiments, track individual and/or organization-wide adherence to such goals. In some embodiments, the wellness scheduling subsystem 202 may report metrics regarding adherence of such goals. In some embodiments, the wellness scheduling subsystem 202 may monitor and/or report deviations from default meeting type designations toward less active meeting type formats. In some embodiments, the wellness scheduling subsystem 202 may require prior authorization, e.g., from a supervisor or the like, before a meeting type designation other than a default meeting type designation may be selected.

Figure 5:
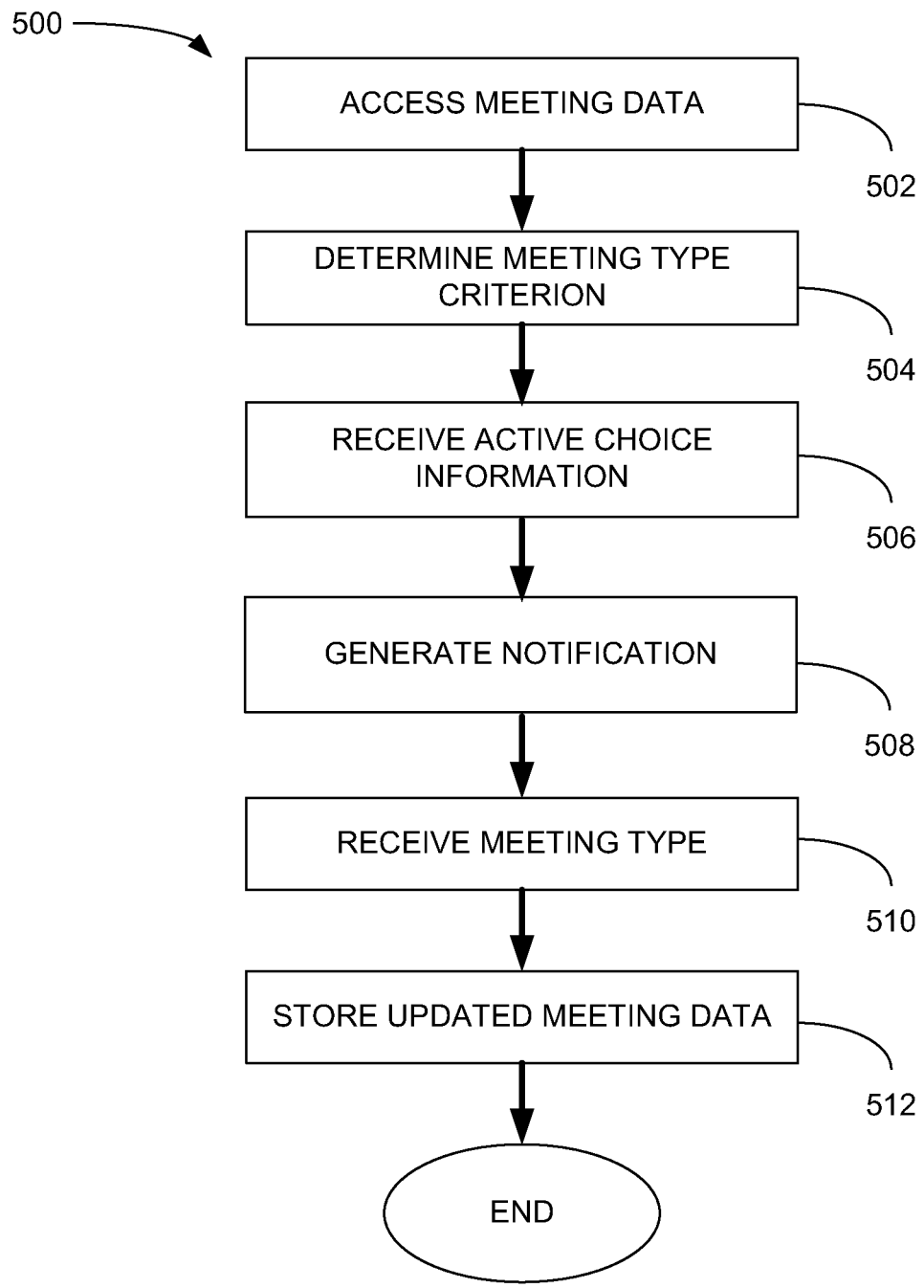
FIGS. 5-7 are process flows illustrating methods for promoting wellness-related behaviors, according to example embodiments.

FIG. 5 illustrates a method 500 for promoting wellness-related behavior using a scheduling system, according to an example embodiment. The method 500 may be performed by the user device 102, partially by the user device 102 and partially be the scheduling management device 106, or may be otherwise performed.

The meeting data 110 associated with a meeting is accessed at block 502. The meeting data 110 as accessed may include the date of the meeting, the beginning time of the meeting, the number and/or identity of the invited attendees at the meeting, the location of the meeting, and/or the anticipated duration of the meeting.

In some embodiments, the accessing the meeting data 110 may include receiving the meeting data. For example, the meeting data 110 may be received from a scheduling application that may be used to schedule a meeting. The meeting data 110 may be received directly from the scheduling application and/or may be received from the scheduling application via the network 104. In some embodiments, accessing the meeting data 110 associated with the meeting includes accessing the meeting data 110 from the database 108.

A meeting type criterion may be determined at block 504. The meeting type criterion may include, for example, a number of invited attendees at the meeting and/or an anticipated duration of the meeting. The meeting type criterion may be determined from the meeting data 110 accessed at block 502. For example, the meeting type criterion may include the number of invited attendees at the meeting and the anticipated duration of the meeting.

Active choice information may be received at block 506. The active choice information may include enterprise active choice information 112 (e.g., which may be applied to multiple individuals within an organization) and/or user active choice information 114 (e.g., which may be applied to one user, or may be applied to a group of users). The active choice information may be accessed, in some embodiments, from the database 108.

In some embodiments, the active choice information may include a rule that for a meeting including three of fewer invited attendees at the meeting, the meeting should be designated as a walking meeting. In such an example, if the meeting data 110 includes three of fewer invited attendees at the meeting, the default meeting type designation may be a walking meeting type. In another example, the active choice information may include a rule that if the anticipated duration of the meeting is between thirty minutes and one hour, the meeting should be designated as a standing meeting. In such an example, if the anticipated duration of the meeting, based on the meeting data 110, is between thirty minutes and an hour, the default meeting type designation may be a standing meeting. The active choice information may include various additional/alternative rules.

A notification requesting a meeting type designation may be generated at block 508. The meeting type designation may include a designation of the meeting as being a walking meeting, a standing meeting, or a sitting meeting. In some embodiments, the notification may be generated and presented to the device operator of the user device 102 while the device operator is scheduling the meeting. In some embodiments, the notification requesting a meeting type designation may be generated and presented to the device operator after the meeting has been scheduled.

In some embodiments, the generation of the notification may include generating a notification suggesting a meeting type designation. Generating the notification suggesting the meeting type designation may include generating the notification based on a meeting type criterion.

In some embodiments, generating the notification suggesting the meeting type designation may include generating the notification based on the meeting type criterion and according to one or more rules. The one or more rules may be included in the active choice information.

The generated notification at block 508 may suggest a default meeting type designation based on the meeting type criterion and the active choice information.

The meeting type designation may be received at block 510. The meeting type designation designates the meeting as a walking meeting, as a standing meeting, or as a sitting meeting. In some embodiments, the meeting type designation may be received in response to the generation of the notification. In some embodiments, the received meeting type designation may include the default meeting type designation, for example if the device operator of the user device 102 does not respond to the notification.

Updated meeting data based on the meeting data and the meeting type designation may be stored at block 512. For example, the meeting type designation may be stored as part of the updated meeting data. In some embodiments, storing the updated meeting data may include storing the updated meeting data in the database 108, for examples as meeting data 110.

In some embodiments, storing the updated meeting data may include allocating resources based on the meeting type designation received at block 510. Resources based on the meeting type designation may include, for example, reservation of an office or conference room without chairs for a standing meeting, a reservation of a walking space for a walking meeting, or the like.

Figure 6:
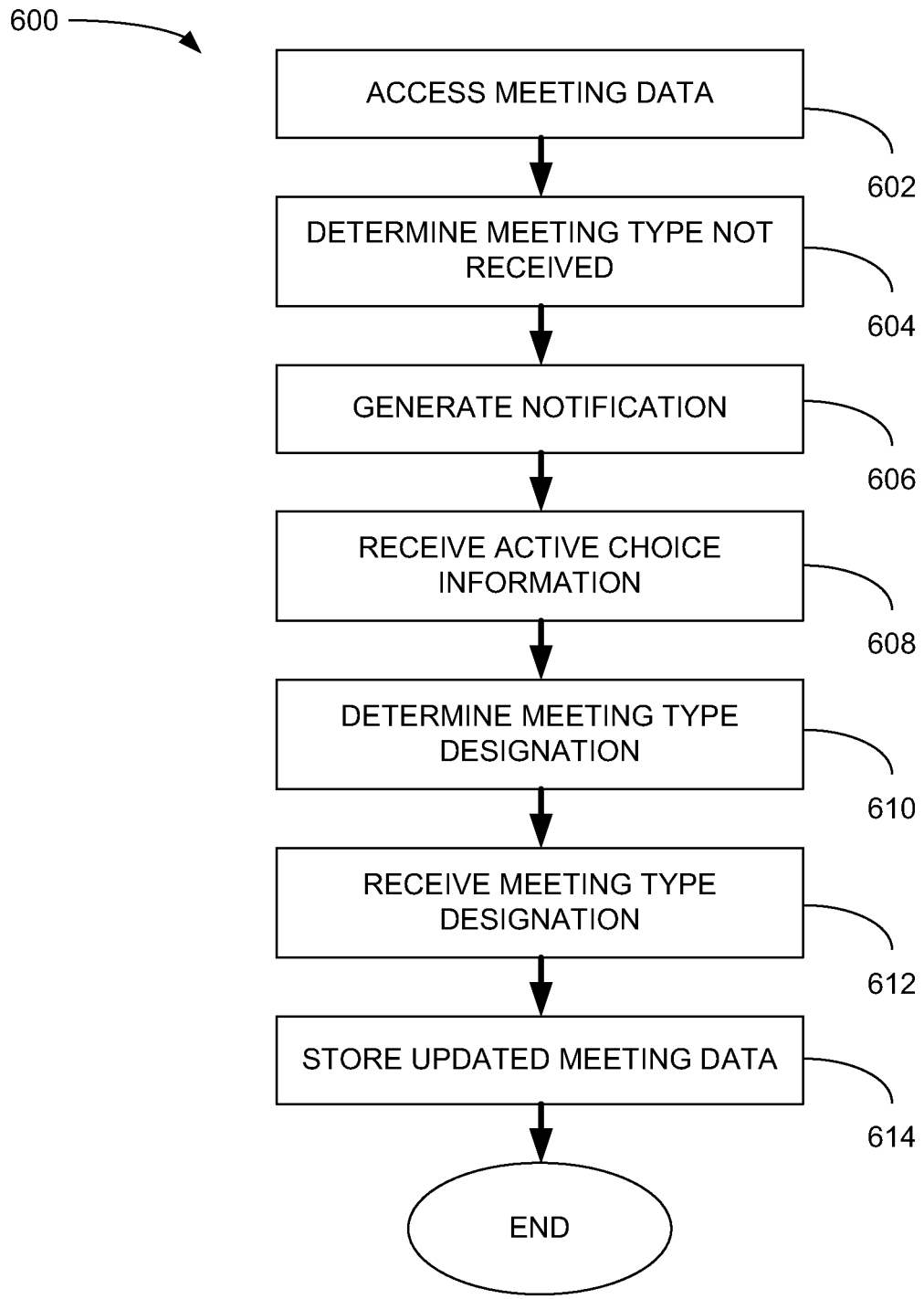

FIG. 6 illustrates a method 600 for promoting wellness-related behavior using a scheduling system. The method 600 may be performed by the user device 102, partially by the user device 102 and partially by the scheduling management device 106, and/or may be otherwise performed.

The meeting data 110 associated with a meeting may be received at block 602.

A determination that a meeting type designation has not been received may be performed at block 604. For example, the device operator of the user device 102 may complete, and/or attempt to complete scheduling the meeting without selecting a meeting type designation.

A notification may be generated at block 606 based on the determination that a meeting type designation has not been received. In some embodiments, the notification may request that a meeting type designation be selected.

Active choice information may be received at block 608. The active choice information may include enterprise active choice information and/or user active choice information. The active choice information may include rules and/or logic for selecting a meeting type designation based on meeting information and/or meeting type criterions, such as a number of invited attendees of the meeting and/or an anticipated duration of the meeting.

A default meeting type designation may be determined at block 610 based on the meeting type criterion and the active choice information. A meeting type designation may be received at block 612. Updated meeting data may be stored at block 614.

Figure 7:
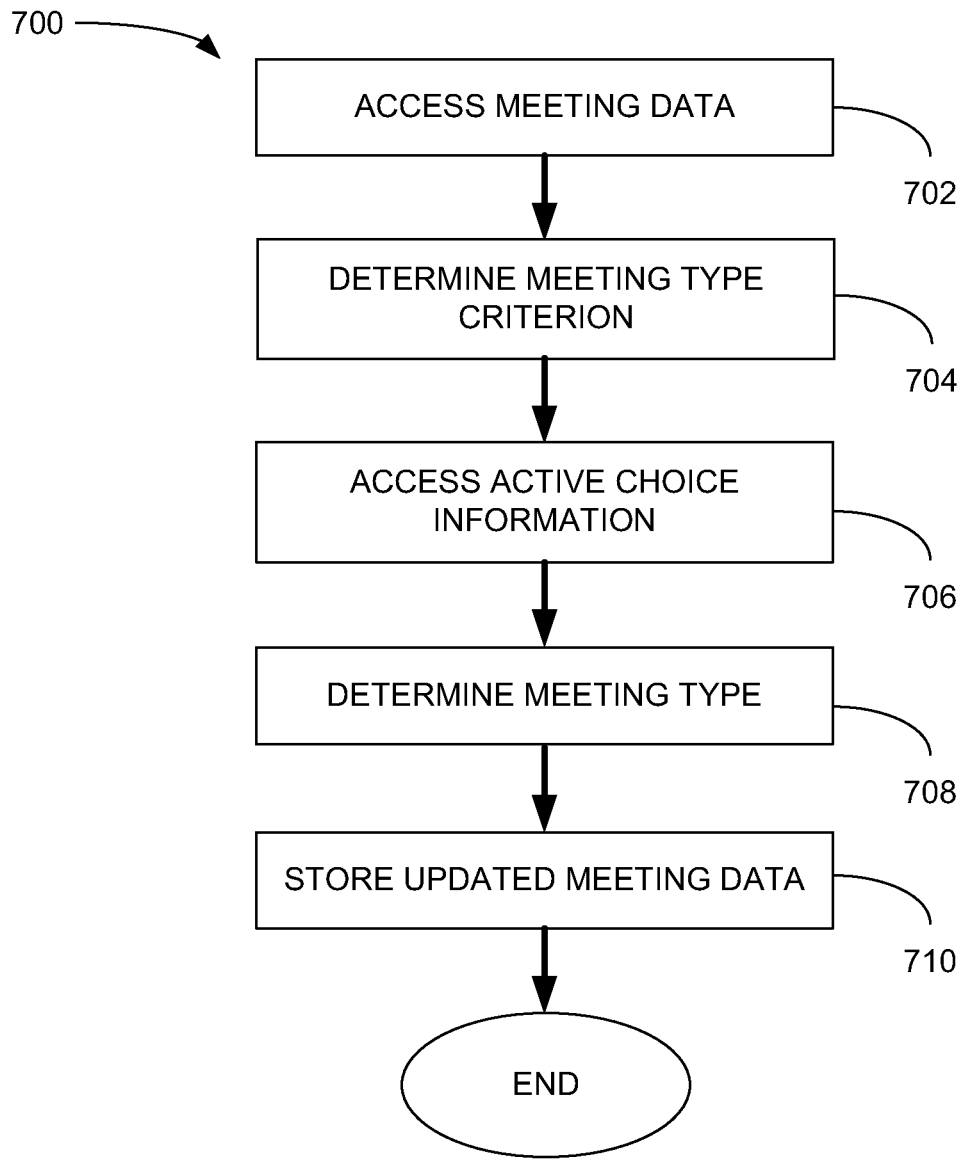

FIG. 7 illustrates a method 700 for promoting wellness-related behavior using a scheduling system. The method 700 may be performed by the user device 102, partially by the user device 102 and partially by the scheduling management device 106, and/or may be otherwise performed.

The meeting data associated with a meeting may be accessed at block 702.

A meeting type criterion may be determined at block 704. The meeting type criterion may include a number of invited attendees at the meeting and/or an anticipated duration of the meeting. A value for the meeting type criterion may be determined based on the received meeting data.

Active choice information may be accessed at block 706. The active choice information may include the enterprise active choice information 112 and/or the user active choice information 114.

A meeting type designation may be determined at block 708. The meeting type designation may be determined based on the meeting data and the meeting criterion. In some embodiments, the meeting type designation may be determined based on the meeting data, the meeting criterion, and the active choice information.

Updated meeting data may be stored at block 710.

Figure 8:
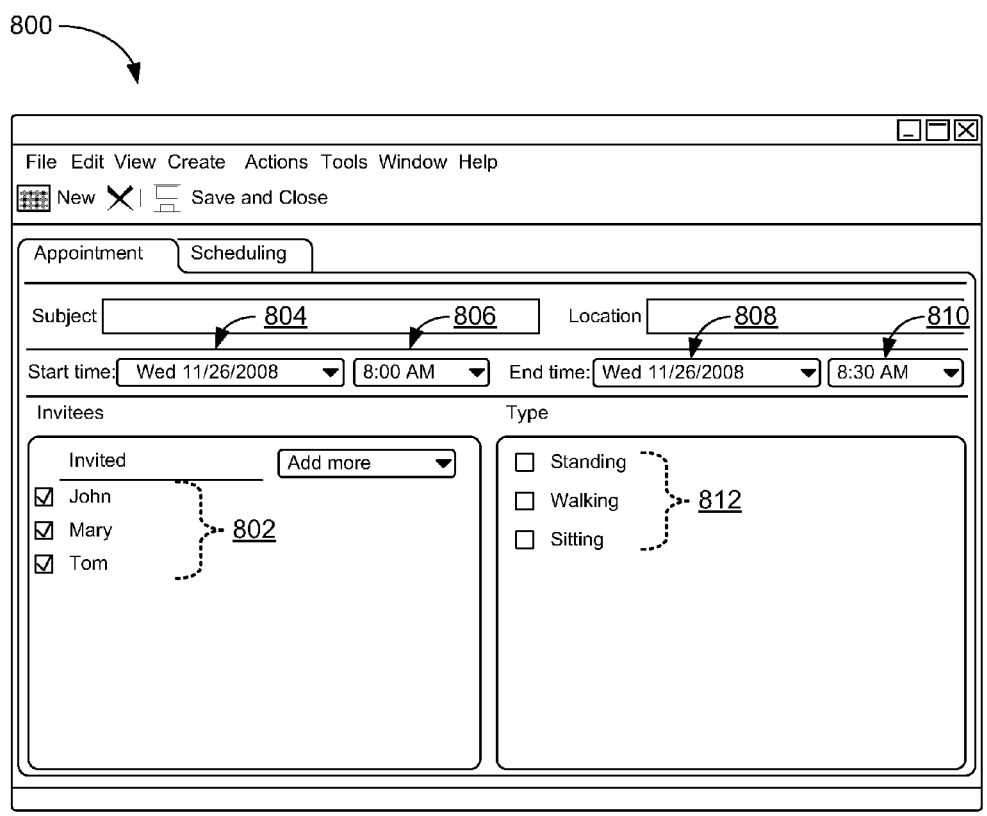
FIGS. 8-10 are example displays, according to example embodiments.
Figure 9:
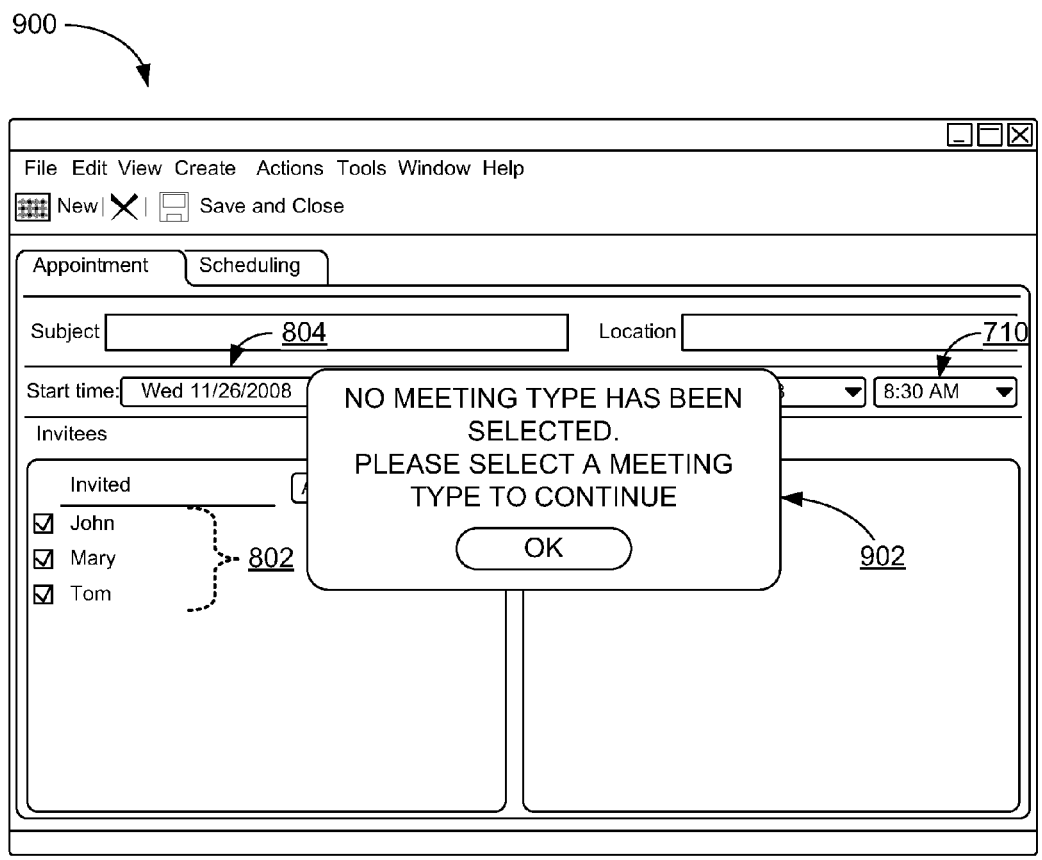
Figure 10:
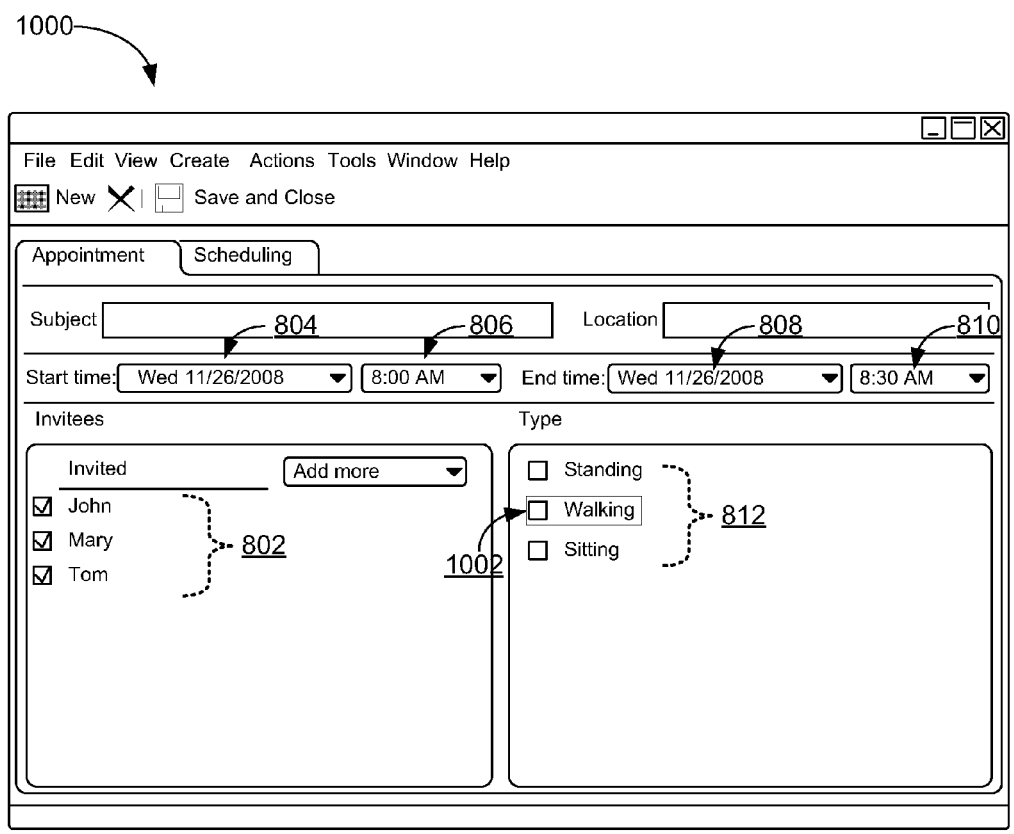

FIGS. 8-10 are example displays 800-1000, according to example embodiments. The displays 800-1000 include example data and may be generated by the wellness scheduling subsystem 202 and ultimately presented to a device operator of the user device 102. However, other types of displays and modification to the displays 800-1000 may additionally or alternatively be presented.

The display 800 of FIG. 8 is an example of a user interface display that may be presented to the device operator of the user device 102 when a scheduling application that incorporates at least a part of the functionality of the subsystem 202 (see FIG. 2) is utilized to schedule a meeting. As shown in the display 800, the device operator is enabled to provide various parameters of a meeting that the device operator wishes to schedule. For example, the display 800 includes an invitee field 802, which may list the invited attendees of the meeting, and may enable the device operator to choose individuals to invite to the meeting. The display 800 may also include a start date field 804 and a start time field 806 that may enable the device operator to provide a desired start date and time of the meeting being scheduled. The display 800 also includes an end date field 808 and an end time field 810 that may enable to the device operator to provide desired end date and time of the meeting being scheduled, thereby enabling the device operator to indicate an anticipated duration of the meeting being scheduled. The display 800 may also include one, or more than one, meeting type designation selections 812. For example, as shown the meeting type designation selections may include check boxes associated with the selections "standing," "walking," and "sitting." The meeting type designation selections may allow the device operator to respectively designate the meeting being scheduled as a standing meeting, a walking meeting, or a sitting meeting. Other selections and selection types may also be utilized. The display 800 may include various other fields that may allow the device operator to provide other parameters of the meeting being scheduled.

In an example embodiment, the selection of a meeting type designation may be required to complete the scheduling of the meeting. If the device operator of the user device 102 tries to complete the scheduling of the meeting without selecting a meeting type designation (e.g., using one of the meeting type designation selections 812) the display 900 of FIG. 9 may be presented to the device operator. The display 900 as shown includes a notification 902 indicating that no meeting type as been selected. The notification 902 may further request that the device operator select a meeting type to continue scheduling the meeting.

In response to the device operator exiting the notification (e.g., by selecting an "OK" button, or otherwise), the display 1000 of FIG. 10 may be presented to the device operator. In an embodiment, the display 1000 may include an indicator 1002 of a default meeting type designation, such as a box around one of the meeting type designations, a highlighting or bolding of one of the meeting type designations, or the like.

In some embodiments, the default meeting type designation may be based on a meeting criterion, such as the number of invited attendees of the meeting, or the duration of the meeting. The default meeting type designation may further be based on a value of the meeting criterion, e.g., which may be provided by the device operator during the scheduling of the meeting. In some embodiments, the default meeting type designation may be based one the meeting type criterion and one, or more than one, rule provided by enterprise active choice information and/or by user active choice information. For example, the default meeting type designation shown in the display 1000 may be based on the meeting type criterion including the number of invited attendees of the meeting, in which a rule included in enterprise active choice information associated with an organization of the which the device operator is a member may include a rule that meetings including three invited attendees of the meeting may be walking meetings by default.

In an example embodiment, the device operator of the user device 102 may select one of the meeting type designation selections 802, allowing the device operator to complete the scheduling of the meeting. In some embodiments, the device operator may complete scheduling the meeting, resulting in the default meeting type selection being selected. In some embodiments, the device operator may select a meeting type designation other than the default meeting type designation (e.g., by selecting a checkbox associated with a desired meeting type designation).

Figure 11:
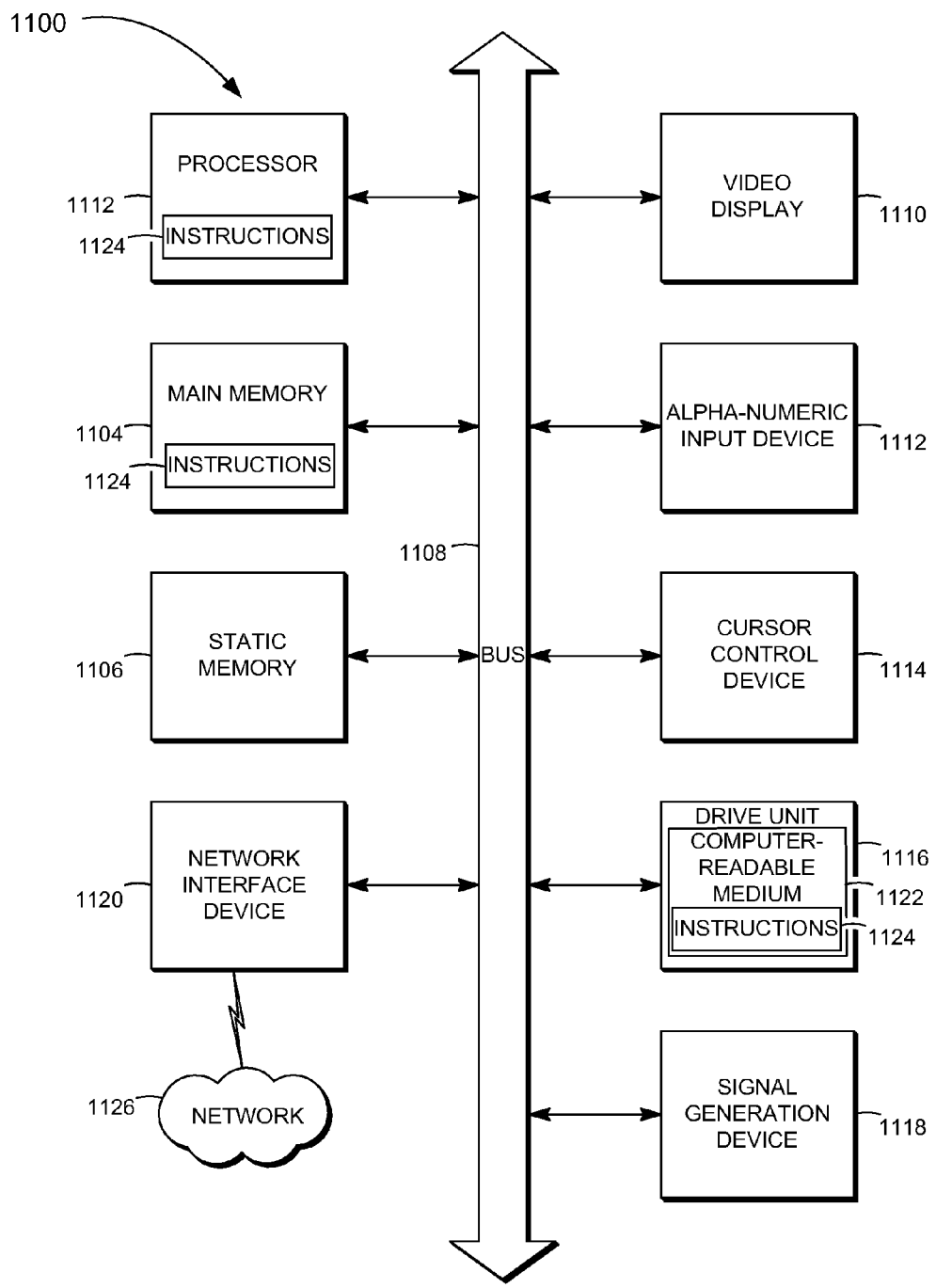
FIG. 11 is a block diagram of a machine in the example form of a computer system within which a set of instructions for causing the machine to perform any one or more of the methodologies discussed herein may be executed or stored.

FIG. 11 shows a block diagram of a machine in the example form of a computer system 1100 within which a set of instructions may be executed causing the machine to perform any one or more of the methods, processes, operations, or methodologies discussed herein. The mobile user device 102 and/or the scheduling management device 106 may include the functionality of the one or more computer systems 1100.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1100 includes a processor 1112 (e.g., a central processing unit (CPU) a graphics processing unit (GPU) or both), a main memory 1104 and a static memory 1106, which communicate with each other via a bus 1108. The computer system 1100 further includes a video display unit 1110 (e.g., a liquid crystal display (LCD) or a cathode ray tube (CRT)). The computer system 1100 also includes an alphanumeric input device 1112 (e.g., a keyboard), a cursor control device 1114 (e.g., a mouse), a drive unit 1116, a signal generation device 1118 (e.g., a speaker) and a network interface device 1120.

The drive unit 1116 includes a computer-readable medium 1122 on which is stored one or more sets of instructions (e.g., software 1124) embodying any one or more of the methodologies or functions described herein. The software 1124 may also reside, completely or at least partially, within the main memory 1104 and/or within the processor 1112 during execution thereof by the computer system 1100, the main memory 1104 and the processor 1112 also constituting computer-readable media.

The software 1124 may further be transmitted or received over a network 1126 via the network interface device 1120.

While the computer-readable medium 1122 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, meeting data associated with a meeting may be accessed. A meeting type designation may be received, in which the meeting type designation may designate the meeting as a walking meeting, a standing meeting, or a sitting meeting. Updated meeting data based on the meeting data and the meeting type designation may be stored.

In an example embodiment, meeting data associated with a meeting may be received. A meeting type designation associated with the meeting may be determined based on the meeting data and a meeting type criterion. The meeting type designation may designate the meeting as a walking meeting, a standing meeting, or a sitting meeting. Updated meeting data based on the meeting data and the meeting type designation may be stored.

In an example embodiment, meeting data associated with a meeting may be received. It may be determined that a meeting type designation has not been received. A notification based on a determination that the meeting type designation has not been received may be generated.

Thus, methods and systems for promoting wellness-related behaviors have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
   accessing, by a processor, meeting data associated with a meeting, the meeting being or to be included on a schedule, the meeting data including participant identification, a number of participants associated with the meeting, and a designated duration of the meeting;
   automatically generating, by the processor, a suggested meeting attendee activity level format based on participant identification, the number of participants associated with the meeting, an organizational defined activity level rule, and the duration of the meeting;
   generating, by the processor, a meeting attendee activity level format display including the suggested meeting attendee activity level format and a plurality of additional meeting attendee activity level formats, the suggested meeting attendee activity level format being a walking meeting format, a standing meeting format, or a sitting meeting format;
   receiving, by the processor, selection of a meeting attendee activity level format designation in response to generation of the meeting attendee activity level format display, the meeting attendee activity level format designation including designation of the walking meeting format, the standing meeting format, or the sitting meeting format; and
   storing, by the processor, updated meeting data based on the meeting data and receipt of the selection of the meeting activity level format designation.

2. The method of claim 1, wherein accessing meeting data comprises:
   receiving the meeting data associated with the meeting.

3. The method of claim 1, wherein accessing meeting data comprises:
   accessing the meeting data from a database.

4. The method of claim 1, further comprising:
   generating a notification requesting selection of the meeting attendee activity level format designation,
   wherein receipt of selection of the meeting attendee activity level format designation is in response to generation of the notification requesting selection of the meeting attendee activity level format designation and generation of the meeting attendee activity level format display.

5. The method of claim 4, wherein generating the notification requesting selection of the meeting attendee activity level format designation is based on the meeting data and a meeting type criterion.

6. The method of claim 5, wherein the meeting type criterion includes a number of attendees at the meeting.

7. The method of claim 5, wherein the meeting type criterion includes an anticipated meeting duration.

8. The method of claim 5, further comprising:
   receiving enterprise active choice information, the enterprise active choice information include the organizational defined activity rule; and
   determining a default meeting type designation based on the meeting type criterion and the enterprise active choice information.

9. The method of claim 5, further comprising;
   receiving user active choice information; and
   determining a default meeting attendee activity level format designation based on the meeting type criterion based and the user active choice information.

10. The method of claim 1, further comprising:
    allocating resources for the meeting based on the meeting attendee activity level format designation.

11. The method of claim 1, further comprising:
    generating a meeting display including indicia of the meeting attendee activity level format designation included in the updated meeting data.

12. The method of claim 1, further comprising:
    assigning a default meeting attendee activity level format designation to the meeting based on a meeting characteristic,
    wherein the meeting data associated with the meeting includes indicia of the default meeting attendee activity level format designation, and the default meeting attendee activity level format designation is different than the meeting attendee activity level format designation.

13. The method of claim 1, further comprising:
    scheduling the meeting based on the updated meeting data.

14. The method of claim 1, wherein meeting data further includes a meeting topic, a meeting date, and a meeting location.

15. The method of claim 1, further comprising:
    generating a deviations report that reflects whether the meeting attendee activity level format designation is the same as the suggested meeting attendee activity level format.

16. A non-transitory machine-readable medium comprising instructions, which, when executed by one or more processors, cause the one or more processors to perform the following operations:
    access meeting data associated with a meeting, the meeting being or to be included on a schedule, the meeting data including participant identification, a number of participants associated with the meeting, and a designated duration of the meeting;
    automatically generate a suggested meeting attendee activity level format based on the participant identification, the number of participants associated with the meeting, an organizational defined activity level rule, and the duration of the meeting;
    generate a meeting attendee activity level format display including the suggested meeting attendee activity level format and a plurality of additional meeting attendee activity level formats, the suggested meeting attendee activity level format being a walking meeting format, a standing meeting format, or a sitting meeting format;
    receive selection of a meeting attendee activity level format designation in response to generation of the meeting attendee activity level format display, the meeting attendee activity level format designation including designation of the walking meeting format, the standing meeting format, or the sitting meeting format; and
    store updated meeting data based on the meeting data and receipt of the selection of the meeting activity level format designation.

17. A system comprising:
    a processor and a memory;
    a meeting data access module deployed in the memory and executed by the processor to access meeting data associated with a meeting, the meeting being or to be included on a schedule, the meeting data including participant identification, a number of participants associated with the meeting, and a designated duration of the meeting;
    a meeting type determination module deployed in the memory and executed by the processor to automatically generate a suggested meeting attendee activity level format based on the participant identification, the number of participants associated with the meeting, an organizational defined activity level rule, and the duration of the meeting;

a notification module deployed in the memory and executed by the processor to generate a meeting attendee activity level format display including the suggested meeting attendee activity level format and a plurality of additional meeting attendee activity level formats, the suggested meeting attendee activity level format being a walking meeting format, a standing meeting format, or a sitting meeting format;

a meeting type receiver module deployed in the memory and executed by the processor to receive selection of a meeting attendee activity level format designation in response to generation of the meeting attendee activity level format display, the meeting attendee activity level format designation including designation of the walking meeting format, the standing meeting format, or the sitting meeting format; and a meeting data storage module deployed in the memory and executed by the processor to store updated meeting data based on the meeting data and receipt of the selection of the meeting activity level format designation.

\* \* \* \* \*